United States Patent
Narasimhan et al.

(10) Patent No.: US 10,902,946 B2
(45) Date of Patent: Jan. 26, 2021

(54) MEDICATION ADHERENCE DEVICE AND COORDINATED CARE PLATFORM

(71) Applicant: WatchRX, Inc., Acton, MA (US)

(72) Inventors: Jayanthi Narasimhan, Acton, MA (US); Arun Buduri, Somerville, MA (US)

(73) Assignee: WATCHRX, INC., Acton, MA (US)

( * ) Notice: Subject to any disclaimer, the term of this patent is extended or adjusted under 35 U.S.C. 154(b) by 759 days.

(21) Appl. No.: 15/158,770

(22) Filed: May 19, 2016

(65) Prior Publication Data
US 2016/0342767 A1    Nov. 24, 2016

Related U.S. Application Data

(60) Provisional application No. 62/164,307, filed on May 20, 2015.

(51) Int. Cl.
*G16H 40/63* (2018.01)
*G06F 1/16* (2006.01)
(Continued)

(52) U.S. Cl.
CPC ............ *G16H 40/63* (2018.01); *G06F 1/163* (2013.01); *G06F 19/00* (2013.01); *G06N 5/04* (2013.01); *G16H 20/10* (2018.01); *G16H 40/67* (2018.01)

(58) Field of Classification Search
USPC ........................................................ 705/2, 3
See application file for complete search history.

(56) References Cited

U.S. PATENT DOCUMENTS 7,751,285 B1 * 7/2010 Cain .................... G04G 9/0017
368/82
7,825,794 B2   11/2010 Janetis et al.
(Continued)

FOREIGN PATENT DOCUMENTS

WO    WO 2016/187374    11/2016

OTHER PUBLICATIONS

Ilias Maglogiannis and Panayiotis Tsanakas, "Mobile Reminder System for Furthering Patient Adherence Utilizing Commodity Smartwatch and Android devices", Jan. 2015 (Year: 2015).*

(Continued)

*Primary Examiner* — Aryan E Weisenfeld
*Assistant Examiner* — Joshua B Blanchette
(74) *Attorney, Agent, or Firm* — Hamilton, Brook, Smith & Reynolds, P.C.

(57) ABSTRACT

A method of supporting user adherence to a medication regimen includes storing received medication information associated with one or more medications using a patient wearable device and a coordinated care platform. The method also includes displaying identification and dosing information associated with the medications, generating a notification indicating that the identification information is being displayed, monitoring a response input indicating that the medications have been administered. For each of the one or more medications displayed, the method includes generating a medication status describing that either (i) the medication has been administered or (ii) the response has not been received. The method further includes generating a reminder notification when the medication status indicates that the response has not been received. The method may further include gathering behavioral data points associated with the user for submission to the coordinated care plat- (Continued)

form, which performs predictive analytics based on the data points.

16 Claims, 10 Drawing Sheets

(51) Int. Cl.
*G06N 5/04* (2006.01)
*G06F 19/00* (2018.01)
*G16H 20/10* (2018.01)
*G16H 40/67* (2018.01)

(56) References Cited

U.S. PATENT DOCUMENTS

| | | | |
|---|---|---|---|
| 8,568,313 B2 | 10/2013 | Sadhu | |
| 9,083,546 B2 | 7/2015 | Sadhu | |
| 2007/0192910 A1* | 8/2007 | Vu | B25J 5/007 700/245 |
| 2011/0224505 A1 | 9/2011 | Sadhu | |
| 2012/0173319 A1* | 7/2012 | Ferrara | G06Q 30/0241 705/14.4 |
| 2013/0002795 A1* | 1/2013 | Shavelsky | A61J 7/04 348/14.01 |
| 2013/0065569 A1* | 3/2013 | Leipzig | H04W 8/22 455/416 |
| 2014/0028456 A1 | 1/2014 | Sadhu | |
| 2014/0073881 A1 | 3/2014 | Sadhu | |
| 2014/0156309 A1* | 6/2014 | Sannoufi | G06F 19/00 705/3 |
| 2014/0278508 A1* | 9/2014 | Akdogan | A61J 7/02 705/2 |
| 2014/0297006 A1 | 10/2014 | Sadhu | |
| 2015/0085624 A1* | 3/2015 | Zamjahn | G06F 19/3456 368/109 |
| 2015/0223705 A1 | 8/2015 | Sadhu | |
| 2015/0280937 A1 | 10/2015 | Sadhu | |
| 2015/0281930 A1 | 10/2015 | Ben-Porath | |

OTHER PUBLICATIONS

Daniel Rosner, Andrei-Tiberiu Jurba, Razvan Tataroiu, Constantin Ilas; "Wearable Medication Reminder Architecture Enhancement." 2015 20th International Conference on Control Systems and Science (Year: 2015).*

International Search Report and Written Opinion of PCT/US2016/033181 dated Aug. 5, 2016 entitled "Medication Adherence Device and Coordinated Care Platform".

Maglogiannis, I. et al "Mobile 1-20 Reminder System for Furthering Patient Adherence Utilizing Commodity Smartwatch and Android Devices", Proceedings of the 4th International Conference on Wireless Mobile Communication and Healthcare, 11 Transforming Healthcare Through Innovations in Mobile and Wireless Technologies, 2014, pp. 124-127.

Kannath, S., Wheats: A Wearable Personal Healthcare and Emergency Alert and Tracking System 11, European Journal of Scientific Research, Sep. 1, 2012 (Sep. 1, 2012), pp. 382-393, XP55291845, Retrieved from the Internet: URL:https:jjwww.researchgate.netjpublication/236268162 Wheats a Wearable Personal Healthcare and-Emergency Alert and Tracking System [retrieved on Jul. 28, 2016].

Remath, S., et al., "Wearable Internet of Things: Concept, Architectural Components and Promises for Person-Centered Healthcare" Proceedings of the 4th International Conference on Wireless Mobile Communication and Healthcare"Transformi NG Healthcare Through Innovations in Mobile and Wireless Technologies", Jan. 1, 2014 (Jan. 1, 2014).

UnaliWear, "Stay Active and Independent" http://www.unaliwear.com/ retrieved from Internet Aug. 18, 2016.

TREATA Smart Solutions—"SmartCare Watch" www.treatasolutions.com retrieved from Internet Aug. 19, 2016.

VEESAG, "Mobile Personal Emergency Response System" http://www.veesag.com/ retrieved from Internet Aug. 18, 2016.

Engadget "PillDrill does smart medication tracking in style" http://www.engadget.com/2016/04/19/pilldrill-smart-medication-tracking/ retreived from Internet Aug. 18, 2016.

International Preliminary Report on Patentability of PCT/US2016/033181 dated Nov. 21, 2017 entitled "Medication Adherence Device and Coordinated Care Platform".

* cited by examiner

Medication Reminders:

By default, the PWD shows time (i.e., "clock mode"). In the clock mode, the patient can tap on the screen once to get a voice message readout of the current time.

When it is time to take a medication

- PWD displays flashing LEDs on the touch screen (LED color coordinated with each medicine)
- When it is time to take medications, the PWD automatically shows the reminders along with voice instructions. Medicine name, image and dosage appears accompanied by a voice message
- The elderly taps the screen to acknowledge taking the meds.
- The PWD updates the backend with the "taken" status and is then reflected on the mobile app's dashboard that their parent has taken their meds on time
- If the elderly didn't respond to the reminder, the PWD tries reminding several times within a span of 1 hour. If the elderly still don't respond to the reminders beyond an hour, a "missed med" status is sent to the backend. The backend then generates an alert to the caregiver via the mobile app
- Upon seeing the missed medication alert, the caregiver can remind their elderly parent using the mobile app. This sends a "remind them again" message to the PWD via the backend and updates the status on mobile app accordingly when taken
- The caregiver can also call the PWD directly from the caregiver app
- The caregiver may also log on to the website to see further details or larger dashboards with weekly status of their elderly
- If the patient does not respond or acknowledge the caregiver's reminder, the caregiver is alerted immediately
- The caregiver now can (from the caregiver application) call the patient directly on the PWD and talk to the patient
- If all communication modes fail the caregiver can follow the protocol to call either the doctor or the emergency directly from the application
- The PWD goes back to clock mode once the reminders are completed Additional options for the patient and caregiver:

- The PWD alerts the caregiver if not worn for a predetermined period of time
- The patient can initiate a call (non-emergency) to the caregiver
- The alerts can be personalized with the family members' voices
- Heart Rate and ECG can be measured periodically using a guided voice
- The patient can enter any OTC medications that they have taken in addition to the prescribed ones

FIG. 5B

1. Initial Setup – from caregiver app
    a. During the initial setup, the caregiver inputs various details on mobile app about their elderly parent as part of creating their profile. A few listed here
        i. Typical wake-up time and Bedtime
        ii. Typical time for meals (breakfast, lunch, snack, dinner)
        iii. Medication details. A few listed here
            1. Medication name
            2. Medication image (snap a pic from the camera and upload)
            3. Dosage (ex., Take 2)
            4. Strength (ex., 500mg)
            5. Frequency (ex., 3 times a day, 7 days a week)
            6. Before or After Meal
            7. Instructions (ex., Take with water, chew the tablet)
        iv. Any other reminders such as ADL reminders, motivational messages
        v. R U OK option with time(s) when to prompt
        vi. GPS Tracking with Geofence information
    b. Using the mobile app, the caregiver then scans the International Mobile Station Equipment Identity (IMEI) of the PWD (using a QR code or barcode on the PWD's box) to associate this PWD with the profile
    c. Then the caregiver activates the PWD for phone and data service
    d. The profile details (along with IMEI association) are uploaded by the mobile app to the backend
    e. When the PWD is powered on, the app automatically starts (Android menu is not visible) and connects to the backend and registers by using the IMEI
    f. By using the IMEI provided by the PWD app, the backend registers the watch to the elderly's profile and sends all the relevant profile data to the PWD
    g. The PWD downloads all the profile data (including images, dosage and medication regimen) and sets up the reminders accordingly. The PWD is now ready to use
    h. The mobile app shows that the PWD is now live and active, along with its battery and signal status

FIG. 7

MEDICATION ADHERENCE DEVICE AND COORDINATED CARE PLATFORM

RELATED APPLICATION(S)

This application claims the benefit of U.S. Provisional Application No. 62/164,307, filed on May 20, 2015, the entire teachings of which are incorporated herein by reference.

BACKGROUND

Medication adherence has been a major concern in the senior age group (e.g., 65 years old and older) for several decades, accounting for one-third of all senior hospital admissions. Medication non-adherence is major contributing factor to health care costs, especially among seniors with multiple chronic conditions. Such seniors often are re-admitted to hospitals due to not following medication regimen, and/or are advised to get admitted to nursing homes, home care or assisted living facilities. The major reasons for non-adherence include forgetting to take their medications and getting confused with the complexity of the medication regimen.

There are relatively few existing solutions available for ensuring medication adherence in elderly patients. Examples include electronic pill packs such as MedMinder™, electronic caps on prescription containers, WisePill, and various smartphone apps. Many of these adherence techniques either blink light emitting diodes (LEDs) or produce a sound (e.g., beep) when it is time to take medicine. A major issue with such designs is that the patient needs to be in close proximity to see the lights or hear the beeps. For example, the patient may miss a reminder if the medication adherence device is in the kitchen while the patient is in the bathroom.

Existing smartphone apps typically generate reminders based on SMS text messaging. Smartphone usage, however, is less than 10% among seniors 75 years and older, and is less than 5% among seniors 80 years and older. Furthermore, many seniors get confused navigating through complex smartphone and app menus, and the apps usually require complex setup through the host smartphone.

Clearly there is a need for a medication adherence solution that is easy to use for seniors with multiple chronic conditions and dexterity, vision and hearing issues.

SUMMARY OF THE INVENTION

The described embodiments include a Coordinated Care System (CCS), which provides a medication adherence solution for patients who are not completely capable of functioning independently. The CCS may include a patient wearable device (PWD), a caregiver mobile app, and a webserver. The webserver implements a coordinated care platform that seamlessly integrates the PWD, the caregiver mobile app, the webserver, and various third party providers (e.g., pharmacy API integration, Electronic Health Records software such as EPIC). The coordinated care platform receives, processes, and analyzes information from the PWD and the caregiver mobile app, to provide status and predictive information to the caregiver and/or other relevant healthcare providers.

In one embodiment, the PWD is a wrist-worn apparatus (or other form such as pendant or armband) with a display screen, audio input and output (e.g., speaker and microphone) and user input mechanisms (e.g., buttons and/or touch-sensitive display screen). The embodiment may include a single System on a Chip (SoC) architecture that includes at least a chronometer (i.e., a watch), a cellular telephone, a GPS receiver, a camera, and one or more sensors (e.g., gyroscope, accelerometer and/or magnetometer).

The described embodiments may provide a dedicated PWD that helps elderly persons remember to take their medication on time, and also assists in various daily life activities and help elderly people remain independent. In the descriptions herein, the person wearing the PWD may be referred to as a "patient"

In some embodiments, a PWD may provide visual and audible medication reminders including a display of medication name, an image of the medication, and dosage with voice instructions, displayed text, or both. Such a PWD may provide substantially constant connectivity to caregivers to allow the caregivers to receive real time status notifications, and a mechanism to call back and immediately check the patient's condition. The PWD may also combine a cellular telephone, GPS tracking and fall detection to provide automatic calling of a caregiver or healthcare professional in an emergency situation.

In general, a PWD may help seniors live independently by assisting them with medication reminders, Activities of Daily Life (ADL) reminders (such as drinking water, eating food and exercising) and enabling them to call their family whenever and wherever they need help. The caregivers are notified with the status and alerts, so they always know the status of the patient. The coordinated care platform integrates personalized treatment programs in situations where the PWD is provided to patients by the treatment providers such as hospitals, pharmacies, or institutional care facilities (such as independent or assisted living). In some embodiments, the PWD may provide a periodic (e.g., daily) "are you okay?" (R U OK) check to the patient.

The described embodiments may provide a single, integrated coordinated care environment (also referred to herein as a coordinated care platform). This coordinated care platform may (i) manage the patient's medication regimen, (ii) coordinate communication between the patient, and the caregiver, and other relevant healthcare professionals, (iii) integrate with pharmacies for automatic download of patient's medication regimen into the PWD, (iv) coordinate updates of the medication regimen from the caregiver and/or the pharmacy, (v) provided an executive dashboard for hospitals to provide an aggregated real-time, current status of the patient, and/or (vi) implement an Early Warning Predictive Analysis (EWPA) of behavioral information captured and conveyed from the PWD.

The behavioral information, based on engagement with the PWD (e.g., tapping the touch-sensitive display to acknowledge taking a medication) and movement/position of the PWD (e.g., patient in a reading position), may include a significant number of behavior points (for example, 250 or more behavioral points). Once the medication reminder sets off, every move by the patient such as lifting the hand, reading the watch, tapping to acknowledge taking the identified medicine, for example, is captured, and captured data is conveyed through the coordinated care platform periodically (e.g., every 15 minutes). The EWPA may compare the captured data to previously received historical data to predict trending, and/or to identify/predict an anomaly. Results of the EWPA may be documented in summaries and/or detailed reports, which may be made available for use by the caregivers, physicians and/or other healthcare providers.

Adverse Drug Reactions (ADRs) are significant factors contributing to emergency situations and increased healthcare costs. Some embodiments may address ADRs by tracking Over-The-Counter (OTC) medications (dosage and time taken) consumed ad hoc by the patient, and evaluating the OTC medications with respect to the prescription regimen being followed by the patient.

In some embodiments the software of the PWD is customizable, which allows for personalized therapy with disease specific intervention messages to the patients; this feature can be used for clinical trials and motivational messages during a therapy along with medication reminders. In some embodiments, the PWD may support automatic setup, and real-time synchronization (i.e., update) of prescription and filled medication information. The distinction between prescription medication and filled medication is that filled medication refers to the medication that was actually filled based on the prescription. For example, the prescription may be for a brand name medicine, while the filled medication may end up being a generic form, in which case the color or dosage may be different from what was actually prescribed. Also, sometimes not all prescribed medications are actually filled, as some of the prescribed can be "as needed" medication.

The described embodiments may provide what amounts to 24 hours per day, 7 days per week (24×7) connectivity of the patient to one or more caregivers, via a mobile app running on a platform such as a smartphone or tablet at the caregiver's location. Such 24×7 connectivity facilitates (i) staying connected with an elderly parent, (ii) getting missed medication and emergency alerts, (iii) receiving a real-time feed of the current status of the patient.

In an application of the described embodiments, the Coordinated Care Platform may be used for Phase 3 clinical trials for new drug application to study the effectiveness of a medication. In Phase 3 clinical trial the medication or treatment is given to large groups of people to confirm its effectiveness, monitor side effects, and collect information such as side effects, pain levels etc. to allow the drug or treatment to be used safely. Currently the clinical trials are monitored based on manual methods such as patients logging into electronic diary and providing feedbacks on side effects during in person visits. This method depends on patient's ability to remember all the information to provide and also all vitals are collected only during in person visits, which can be very expensive. The PWD in the described embodiments can be used to (i) convey medication reminders with instructions, (ii) record feedback and side effects and (iii) collect vitals data from Blood Glucose, Blood Pressure and heart rate monitors and provide the data in real time. Use of the described embodiments may also help to reduce patient "in-person" visits and reduce cost of clinical trials.

In another application of the described embodiments, the Coordinated Care Platform may be used for providing targeted therapy for conditions such as ADHD, substance abuse (e.g., smoking cessation), where in addition to a medication regimen, motivational messages are also needed for continued treatment, as well as improving effectiveness of the treatment. As part of the treatment plan, the content of the messages and the schedule can be provided to the coordinated care platform, and then the coordinated care platform can download the messages and schedule to the PWD, to be delivered to the patient at the appropriate time.

In one aspect, the invention may be a method of supporting adherence, of a user, to a medication regimen. The method may include, by a wearable computing device capable of stand-alone, independent operation, the wearable computing device including a display and an embedded cellular transceiver, storing received medication information that characterizes one or more medications, including at least identification information and dosing information, associated with each of the one or more medications. The method may further include displaying identification information and dosing information associated with at least one of the one or more medications. The method may also include generating an initial notification indicating that the identification information is being displayed. The method may also include monitoring a response input instrumentality configured to receive a response indicating that the at least one of the one or more medications has been administered. The response input instrumentality may include, for example, a touch-sensitive display screen or a pushbutton on the PWD. The method may further include, for each of the one or more medications displayed, generating a medication status describing that either (i) the medication has been administered or (ii) the response has not been received.

One embodiment may further include generating a reminder notification when the medication status indicates that the response has not been received, by re-displaying identification information and dosing information associated with one or more medications referenced in the reminder, generating a subsequent notification indicating that the identification information is being displayed, monitoring the response input instrumentality, and, for each of the one or more medications referenced in the reminder, generating an updated medication status describing that either (i) the medication has been administered or (ii) the response has not been received.

Another embodiment may further include repeating the reminder notification periodically until (i) all of the at least one medications have been administered, or (ii) a predetermined time period has elapsed since generation of the initial notification.

Another embodiment may further include providing the reminder notification by playing a voice recording generated by a caregiver. One embodiment may further include repeating the reminder notification at intervals of about 10 minutes. Yet another embodiment may further include notifying a caregiver after the predetermined time period has elapsed.

One embodiment may further include detecting an incoming communication from a caregiver, generating a notification of the incoming communication, and monitoring an incoming communication acceptance input instrumentality configured to receive an accept response that causes the wearable computing device to accept the incoming communication.

Another embodiment may further include automatically accepting an incoming telephone call when the incoming communication acceptance input instrumentality does not receive an accept response within a predetermined time interval.

In one embodiment, the incoming communication may be an R_U_OK alert.

Another embodiment may further include automatically connecting to a healthcare device, receiving health information from the healthcare device, storing the health information and forwarding the health care information to a caregiver. Such a healthcare device may include, for example, a blood glucose meter, a blood pressure measuring device, a weight measurement device (i.e., a scale), or a pulse measuring device. Other such vitals measuring devices may also provide data to the wearable computing device.

In one embodiment, the identification information and dosing information include an image associated with the at least one of the one or more medications, the image including a depiction of a vehicle in which the medication is administered, the vehicle instantiated a number of times corresponding to the dosing information. The vehicle may include a pill, a capsule, or other such vehicles known in the art for conveying medication to a patient.

One embodiment may further include activating a camera integrated into the wearable computing device, the activating occurring in response to a camera stimulus. In one embodiment, the camera stimulus includes one or more of (i) a camera activation communication received from a caregiver, (ii) the medication status indicates that the response has not been received.

One embodiment may further include synchronizing the wearable computing device by receiving and storing updated medication information. Another embodiment may further include determining geolocation of the wearable computing device in relation to a predetermined area, and notifying a caregiver when the geolocation is determined to be outside of the predetermined area.

One embodiment may further include detecting that the user has fallen by analyzing an output of one or more accelerometers embedded in the wearable computing device, and notifying a caregiver upon detecting that the user has fallen.

In another aspect, the invention may be a method of monitoring and analyzing behavior of a patient, and providing predictive analytics therefrom, comprising, by a coordinated care system including a patient wearable device (PWD), a caregiver application and a webserver, gathering, by the PWD, behavioral data associated with the patient and conveying the behavioral data from the PWD to the web server. The method may further include analyzing, by the webserver, the behavioral data to determine one or more behavioral trends. The method may further includes comparing the determined behavioral trends to one or more historical behavioral information to identify a behavioral anomaly. The method may further include sending an alert to the caregiver application when a behavioral anomaly is identified.

In one embodiment, analyzing the behavioral data includes determining a compliance index and an engagement index using an exponential weighted moving average.

In another embodiment, the behavioral data includes one or more of position information based on sensor outputs, response information based on reaction of the patient to reminder information, and vitals information (such as weight, heart rate, blood pressure, blood glucose level, for example) collected by the PWD.

Another embodiment further includes determining, based on the behavioral data, that an emergency event has occurred, and in response to the determining, notifying appropriate emergency response personnel.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 5B shows an outline of an example medication reminder process according to the invention.

FIG. 7 illustrates an outline of an example setup procedure of a PWD according to an embodiment of the invention.

DETAILED DESCRIPTION OF THE INVENTION

A description of example embodiments of the invention follows.

The teachings of all patents, published applications and references cited herein are incorporated by reference in their entirety.

Figure 1:
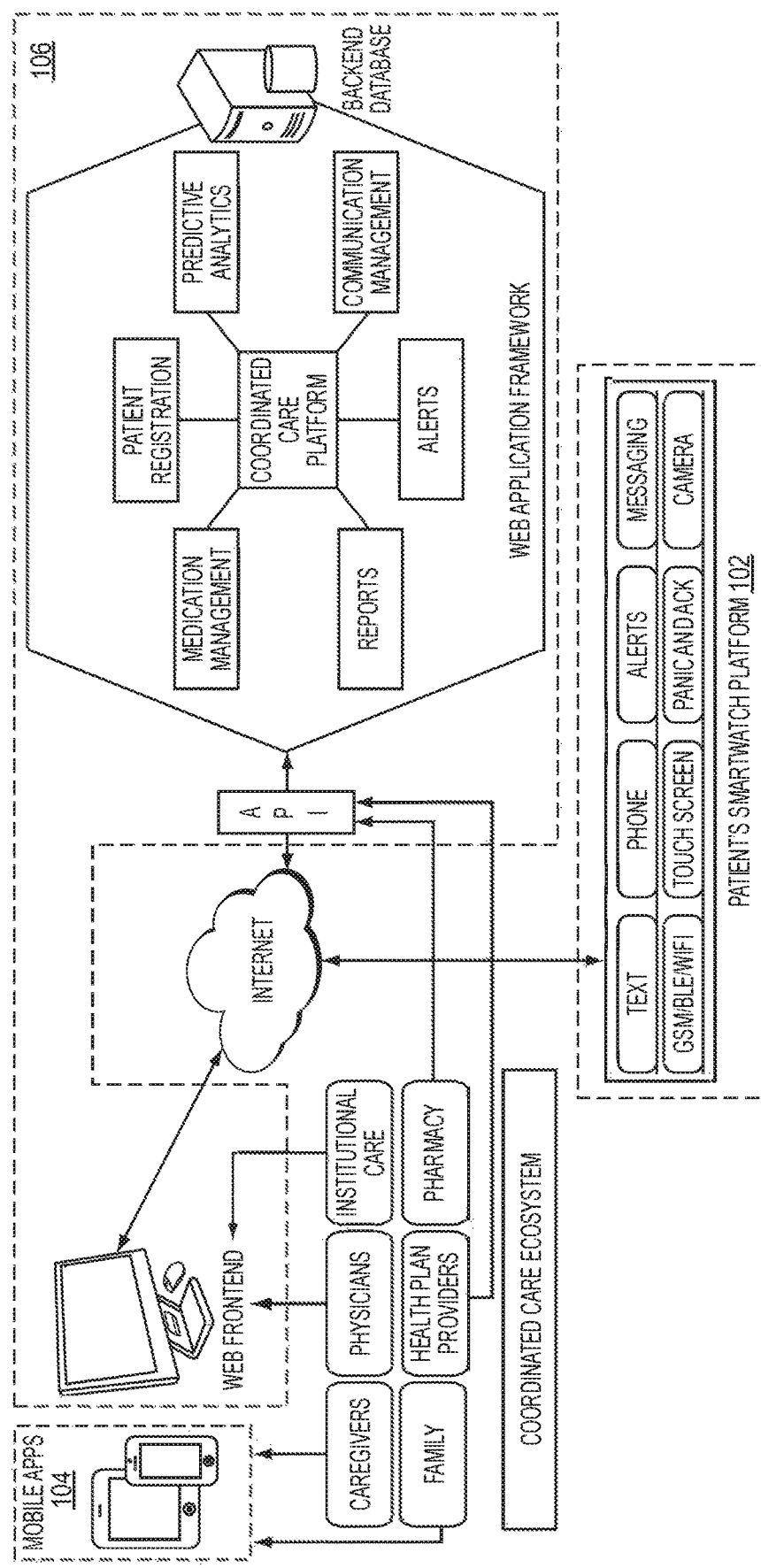
FIG. 1 shows an example embodiment of a coordinated care system according to the invention.

An example embodiment of a Coordinated Care System (CCS) 100, shown in FIG. 1, includes a patient wearable device (PWD) 102, a caregiver mobile app 104, and a webserver 106. The caregiver mobile app 104 runs on a commercially-available platform such as a smartphone or electronic tablet. The webserver 106, which runs on a commercially-available platform such as a computer system or workstation, implements a coordinated care platform that seamlessly integrates the PWD, the caregiver mobile app, the webserver, and various third party providers (such as pharmacies and healthcare providers). The webserver 106 includes a web frontend, a server backend, a backend database and an application program interface (API). Target users for each of these components are shown in Table I.

TABLE I

| Component | Target User |
|---|---|
| Patient Wearable Device (PWD) | Patient |
| Smartphone or Tablet application (Caregiver Mobile App) | Nurse/Caregivers, Family members, Physicians, Medical Coordinators, among others |
| Webserver, backend application with a web frontend | Family members, Physicians, Hospitals, Pharmacy, Caregivers, among others |

The software stack technologies for the CCS components and sub-components are shown in Table II.

TABLE II

| Component | Technology | Target User | Hosted/Runs On |
|---|---|---|---|
| PWD Mobile App | Android Android, iOS | Patient Caregiver | PWD hardware Caregiver's mobile device (smartphone or tablet) |
| Server Backend | Java, Hibernate | CSS Admins | Google App Engine |

TABLE II-continued

| Component | Technology | Target User | Hosted/Runs On |
|---|---|---|---|
| Web Frontend | HTML5, CSS3 | Medical Staff, Admin, Physicians | Google App Engine |
| Backend Database | Google CloudSQL | CSS Admins | Google App Engine |
| API | Java | Mobile apps, Frontend, Pharmacy integration | Google App Engine |

Patient Wearable Device (PWD)

As described below, the PWD 102 supports cellular communications, which enables connection to the webserver 106 through mobile Internet. A SIM card within the PWD 102 is associated with a voice and data plan activated for calls with caregivers and selected family members. As the PWD connects to the webserver 106 using cellular data service, there is no need for external/additional controller, hub or a smartphone in the patient's home or carried by the patient for the PWD to connect to the internet. The PWD is fully functional by itself, and can therefore be used anywhere inside or outside the home, as long as cellular connectivity is available.

The PWD is water resistant with Ingress Protection (IP) IP67 or IP68 certification, so it can be used in the shower, kitchen or rain, even while travelling or sleeping. The first digit 6 in IP67 implies that it is dust proof and the second digit 7 implies water resistant and 8 implies water proof. These certifications are provided International Electrotechnical Commission (IEC) based on tests, and show that the device has proper sealing and enclosures to protect from dust or water.

Patients using the PWD are expected to be seniors typically 70 years or older. In one embodiment, the PWD and its patient interface may be developed with characteristics specifically targeted for this age group to accommodate their attendant vision and dexterity issues.

Figure 2:
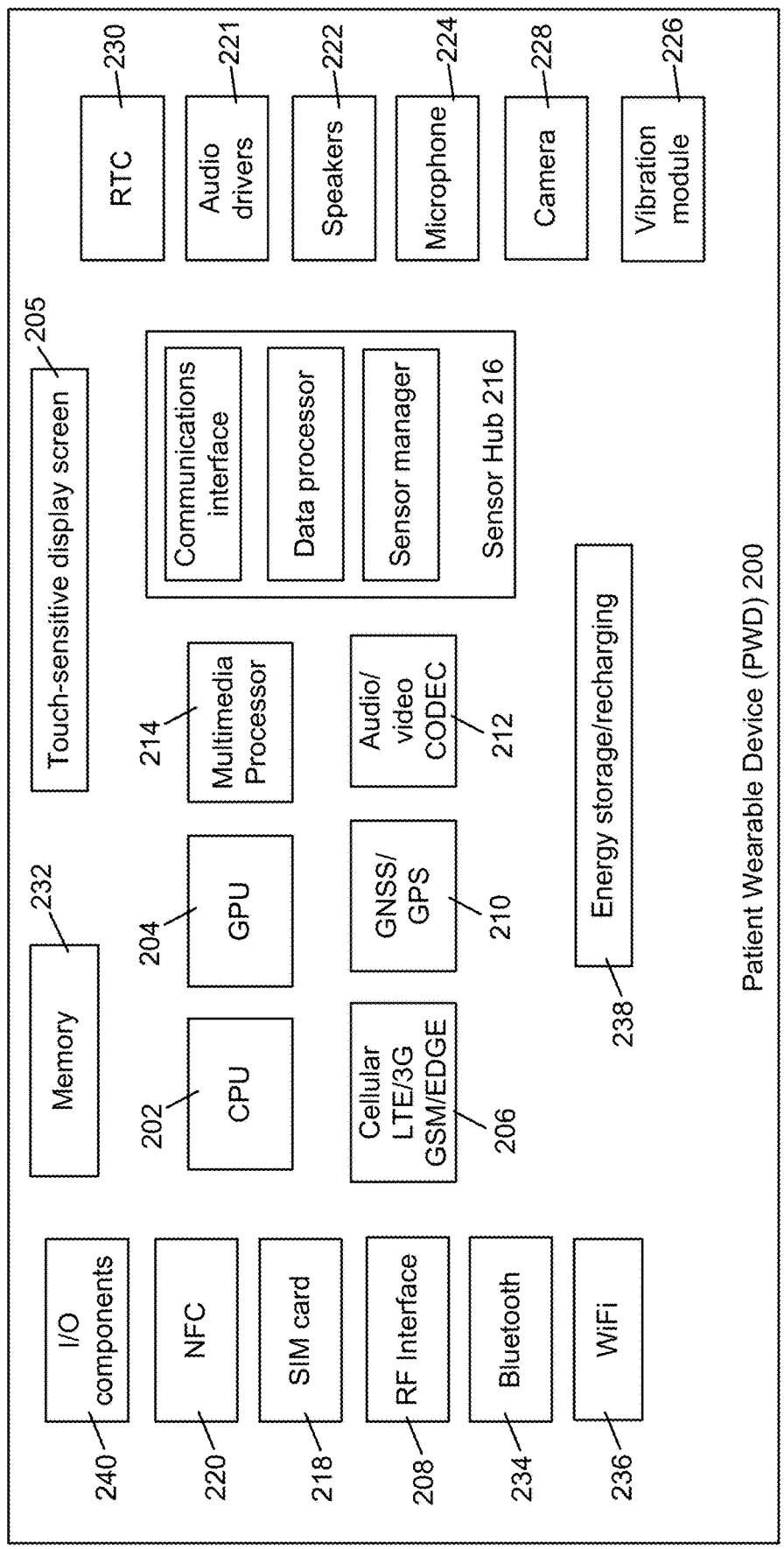
FIG. 2 shows a block diagram view of an example embodiment of a PWD according to the invention.

As shown in FIG. 2, an example embodiment of the PWD 102 may include a Central Processing Unit (CPU) 202, Graphical Processor Unit (GPU) 204, and a touch-sensitive display 205. The display 205 is capable of presenting configurable color schemes that optimizes the visual effect experienced by the patient. In some embodiments, the screen is relatively large (e.g., 1.5 inches by 1.5 inches). Displayed text font is generally large and bold so that elderly patients will have an easier time reading the text. As described herein, patients may respond to medication reminders by tapping the display screen. For such responses, the user can tap the display screen at any point on the surface of the display screen, rather than a specific sub-region of the screen.

The PWD 102 may also include a cellular modem module 206, supporting, for example LTE protocols, 3GPP protocols, GSM/EDGE protocols, combinations thereof, or other wireless wide area communication protocols. The cellular modem 206 coordinates with an RF interface 208 for connection to a cellular wireless network.

The PWD may also include a Global Navigation Satellite System/Global Positioning System (GNSS/GPS) module 210 to determine the position of the PWD 102 based on satellite communication, although other positioning systems known in the art may also be used. The PWD 102 may also include audio and video CODECs 212 for encoding and decoding voice and video information. The PWD 102 may also include a multi-media processor 214 for supporting PWD activities such as voice calls, PWD activation, video calls, playing video, among others.

A sensor hub 216 manages and collects data from one or more sensors (e.g., an accelerometer, a magnetometer, a motion sensor, a gyroscope, a stress/strain sensor, and a pressure sensor, among other types of sensors know in the art). The sensor hub 216 samples data from the one or more sensors and stores the collected information in memory 232. Software or firmware, stored in memory 232 and executed by the CPU 202, may cause data to be extracted from the memory 232, assembled into a predetermined format, and sent to the back-end server within the CCS for various types of processing, such as the Early Warning Predictive Analysis (EWPA) described herein. The sensor hub 216 may be implemented by a processor running instruction code, a collection of analog and digital circuitry, or a combination of both.

The PWD memory 232 may also be used to implement a database to store medication regimen, instructions and messages. In an example embodiment, the following attributes may be stored for each medicine:

Timeslot (i.e., times when the patient takes Breakfast, lunch, snack, dinner, wake up time and bed time)
Medicine name
Dosage (quantity—e.g., two tablets, one capsule, one-half fluid ounce)
To be taken before or after food
Days of week (e.g., every day, every other day, once per week)
Image information for depicting/displaying the medicine
Voice instructions In one example embodiment, the memory 232 is approximately 4 GB. The memory 232 may be implemented in a single memory component, or distributed across two or more memory components. The information that needs to be stored is less than 1 GB including, the medicine image information. Having a local storage in the PWD 102 also helps in delivering the reminders consistently while reducing the risk of failure due to a communication outage between the PWD 102 and the webserver 106. Thus, once the medication details are downloaded to the PWD 102, the PWD 102 may operate substantially autonomously, without requiring constant supporting communication with the webserver 106.

The main functionality of the PWD is implemented with a PWD app. In one embodiment, the PWD app is instruction code, stored in the memory 232 and executed by CPU 202. In one embodiment, the PWD app is a dedicated (kiosk mode with root access) application using Android OS and Android application framework. The term "dedicated" as used herein implies that there are no other applications running on the watch and the user need not navigate through any menus or apps.

To send "medication taken" status, alerts, behavioral data points, and other such information, however, the PWD 102 does communicate with the webserver 106 to some extent. The watch communicates using JAVA REST APIs to the webserver 106. Such communications may be done in the background, without interfering with the PWD's regular functions such as providing medication reminders and collecting behavior data points. In some embodiments, the webserver 106 may periodically check the health of the PWD 102, and the status of its communication capabilities, by executing diagnostic tests. Such diagnostic tests may be executed external to the PWD 102 (e.g., by sending test messages from the webserver 106 to the PWD and requiring specific responses), internal to the PWD (e.g., test instructions stored within the PWD memory 232 and executed by a PWD processor).

In addition, the PWD 102 supports a subscriber identification module (SIM) 218 for designating phone and data service subscriptions, a near-field communication (NFC) module 220 for reading and processing NFC tags, one or more audio drivers 221 and speakers 222 for producing audible sounds, one or more microphones 224 for receiving audible sound and transducing the sound into an electrical signal, a vibration module 226 for providing haptic notifications, one or more cameras 228 and a real time clock (RTC) 230 that provides a chronometer function for date and time of day (i.e., the PWD functions as a wrist watch). The PWD may further include local communications elements such as a Bluetooth transceiver 234 and a WiFi transceiver 236. Other communications protocols (e.g., Zigbee) may also be used.

The PWD 102 may also include an energy storage element (e.g., a lithium-ion battery or other re-chargeable battery type) and associated recharging circuitry 238 for efficiently recharging the energy storage element. Some embodiments provide for an electrical connection of the PWD 102 to a charging unit through electrically conducting contacts. Other embodiments provide for inductive coupling of the PWD 102 to a charging unit.

Information from the patient (e.g., responses to medication reminders) may be provided to the PWD 102 through the touch-sensitive display screen 205, or through other input/output (I/O) components 240, for example push-buttons, sliding switches, and other I/O components known in the art.

In one embodiment, all of the components of the PWD 102 may be implemented by a commercially-available single System On a Chip (SoC) solution. In other embodiments, the functionality may be implemented by a custom-designed device (i.e., ASIC) or chipset, or as combinations of both a commercially-available SoC and custom designed components.

Interaction between the PWD and the patient (i.e., the PWD user interface) is simple. There is no patient-involved setup required for the PWD, as the set up will be completed by the caregiver using the caregiver mobile app (described later herein) or by the pharmacist once the pharmacy is integrated with the CCS.

Activation of the PWD may also be done by the caregiver using the caregiver mobile app. The PWD downloads the complete medication regimen when the PWD is powered on, and the patient can start wearing the PWD once activated. Typically the only action required by the patient is to acknowledge an instruction by performing a single tap anywhere on the display screen. Many aspects of the user interface, including the voice, display and the vibrations, can be customized remotely from caregiver mobile app.

Figure 3:
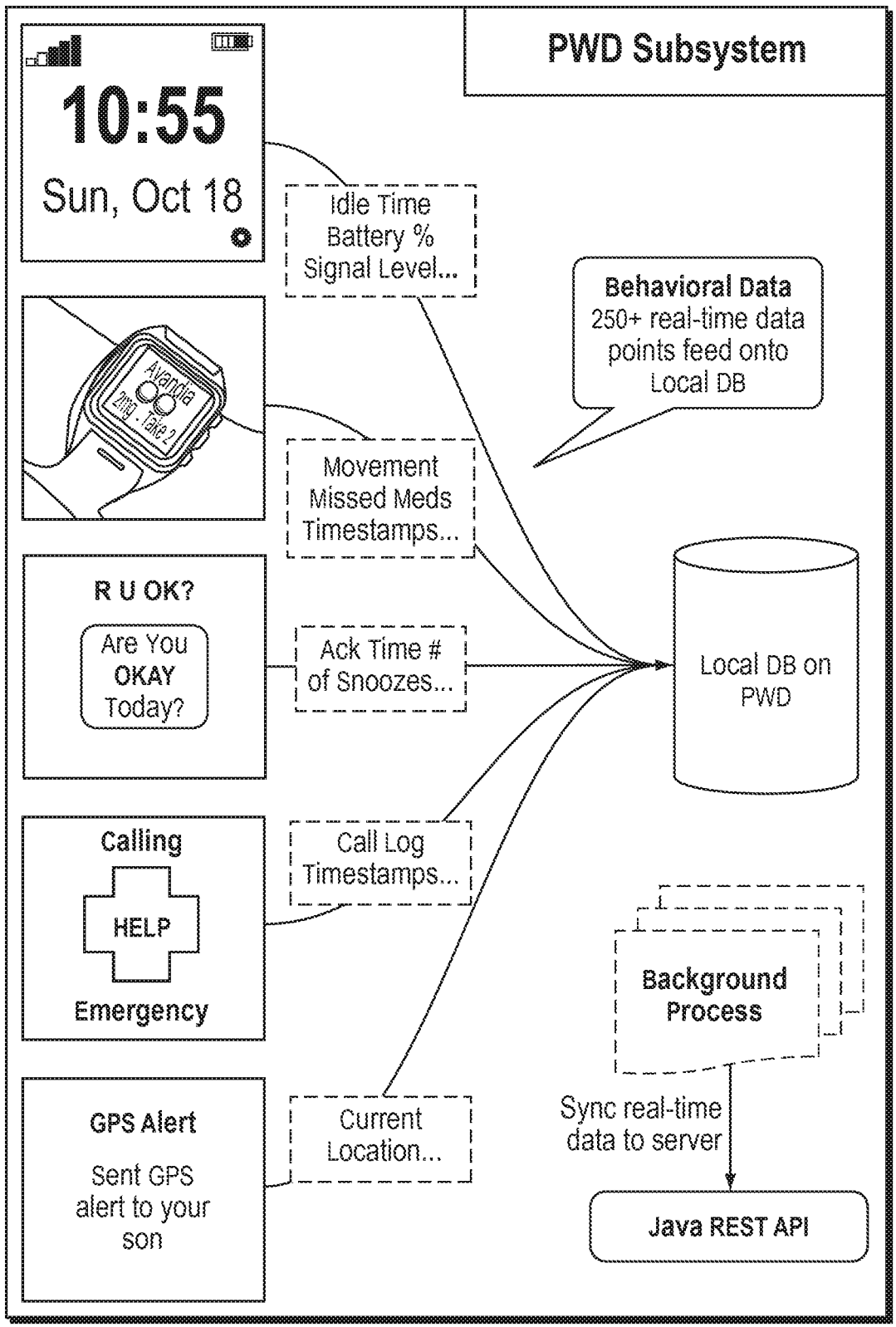
FIG. 3 shows example usage of an embodiment of the PWD shown in FIG. 2.

An example embodiment of a PWD constructed according to the invention, with various screenshots, features and PWD app architecture, is shown in FIG. 3. As shown, the PWD has a local database where the medication regimen, images, and voice files are stored. The local processor activates reminders based on a scheduler, and stores responses from the patient. When the reminders are completed, the PWD sends an alert or log to the coordinated care platform at the webserver, including all the medications taken and missed, along with the time sequence information associated with the responses. The PWD may communicate with the coordinated care platform via JAVA REST APIs. For example a missed medication alert may have following information:
AlertID:
missedTimestamp:
patientID:
missedTimeSlot:
missedBeforeOrAfterFood:
missedMedicationIDs: [{medication detail 1}, {medication detail 2}, {medication detail 3}

Medication details may include, for example, medicine name and dosage, among other descriptive information. Since patientID is in the form of a control number, no name will be sent across.

Figure 4:
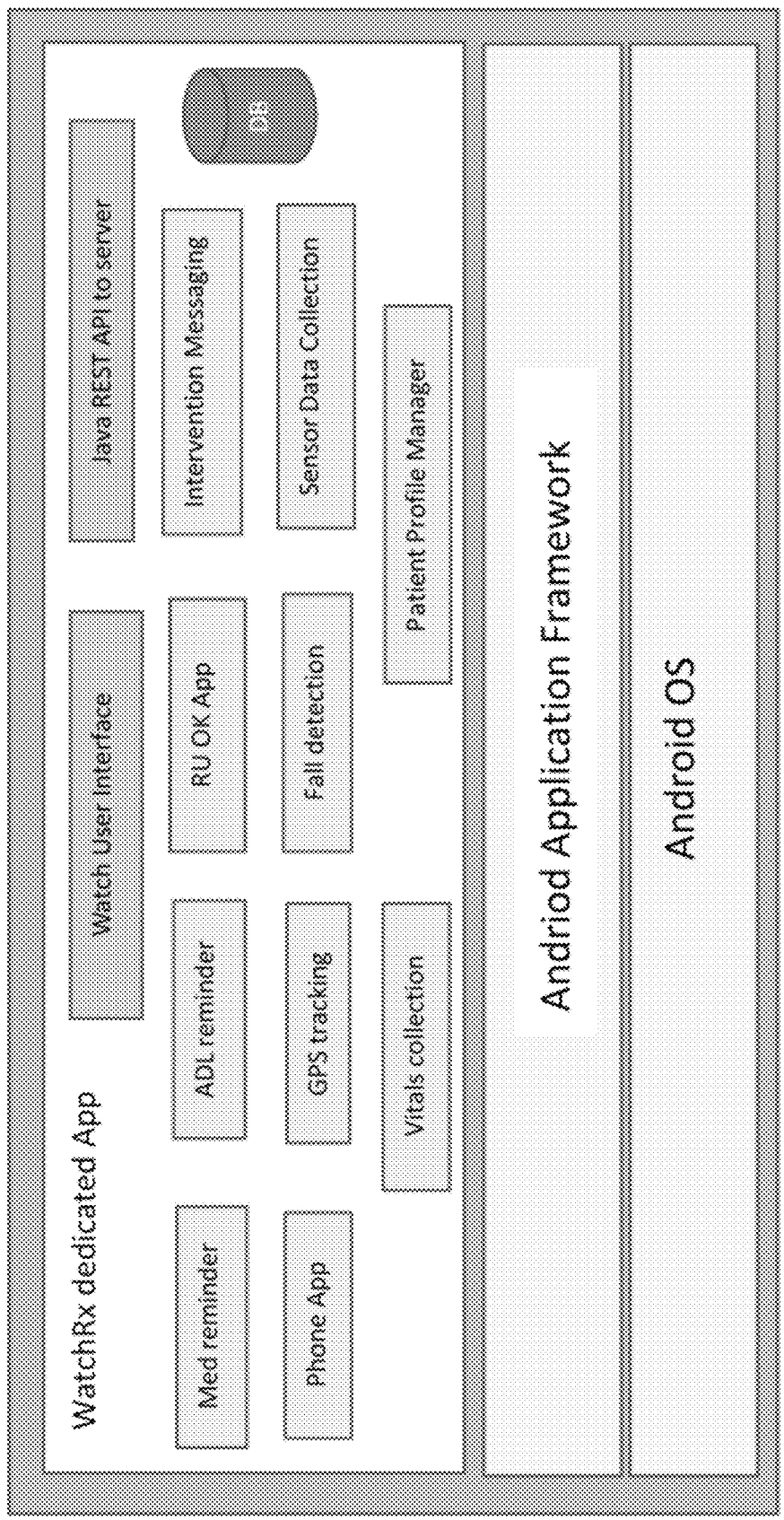
FIG. 4 illustrates a functional block diagram of an example embodiment of the PWD shown in FIG. 2.

FIG. 4 illustrates a functional block diagram of an example embodiment of the PWD 102. An example embodiment of a PWD 102 may provide one or more of the functionalities described below.

Displaying Time of Day—This is the default image displayed by the display screen 105. Time of day (TOD), as described herein, may include hours, minutes, seconds, month, day and year. The PWD may also speak the TOD when the patient taps the display screen (or otherwise indicates a desire to receive an audible version of the TOD). In some embodiments, the patient is able to modify the TOD setting only, with no other menus or navigation requirements.

Providing cellular telephone service—The PWD includes a cellular telephone that supports incoming and outgoing calls. In one embodiment, the PWD cellular telephone is implemented with a commercially available chip set such as the MediaTek 6753 or Qualcomm Snapdragon 2100. These chipsets may support one or more of 3GPP, LTE and GSM/EDGE protocols.

A SIM card is also provided for phone/data service. The SIM card is configured to include a set of preprogrammed telephone numbers and to accept calls only from those numbers. The PWD manages the incoming calls and outgoing calls from the PWD. In one embodiment, the patient is able to call pre-programmed family members by simply pushing a button on the side of the PWD. In one embodiment, a caregiver can program a sequence of telephone numbers and sequentially call each subsequent telephone number if the previous telephone number is not answered.

Providing Medication Reminders—With trio feedback (audio/visual/haptic), the PWD 100 may vibrate, beep and display a "Reminder" screen according to the patient's medication dosing schedule, although other embodiments may present alternative haptic, audio and/or visual stimuli. In response to an acknowledgement from the patient (i.e., the patient tapping the touch-sensitive display screen 105 or pressing a button, depending on the embodiment used), medications are displayed on the display screen 105 one by one, with brand and medication name, medication dosage and strength, an image of the medication, and a voice prompt providing instructions associated with the medication (e.g., how the medication should be taken). If a pill pack with weekly slots is used instead of individual pill bottles, then the image and dosage instructions for the slot may be displayed.

In some embodiments, the voice prompt is customizable to any family member voice. Some patients, especially Alzheimer or Dementia patients, are accustomed to only a family member's voice, so that instructions presented in the family member's voice helps the patient in taking their medicines.

Figure 5A:
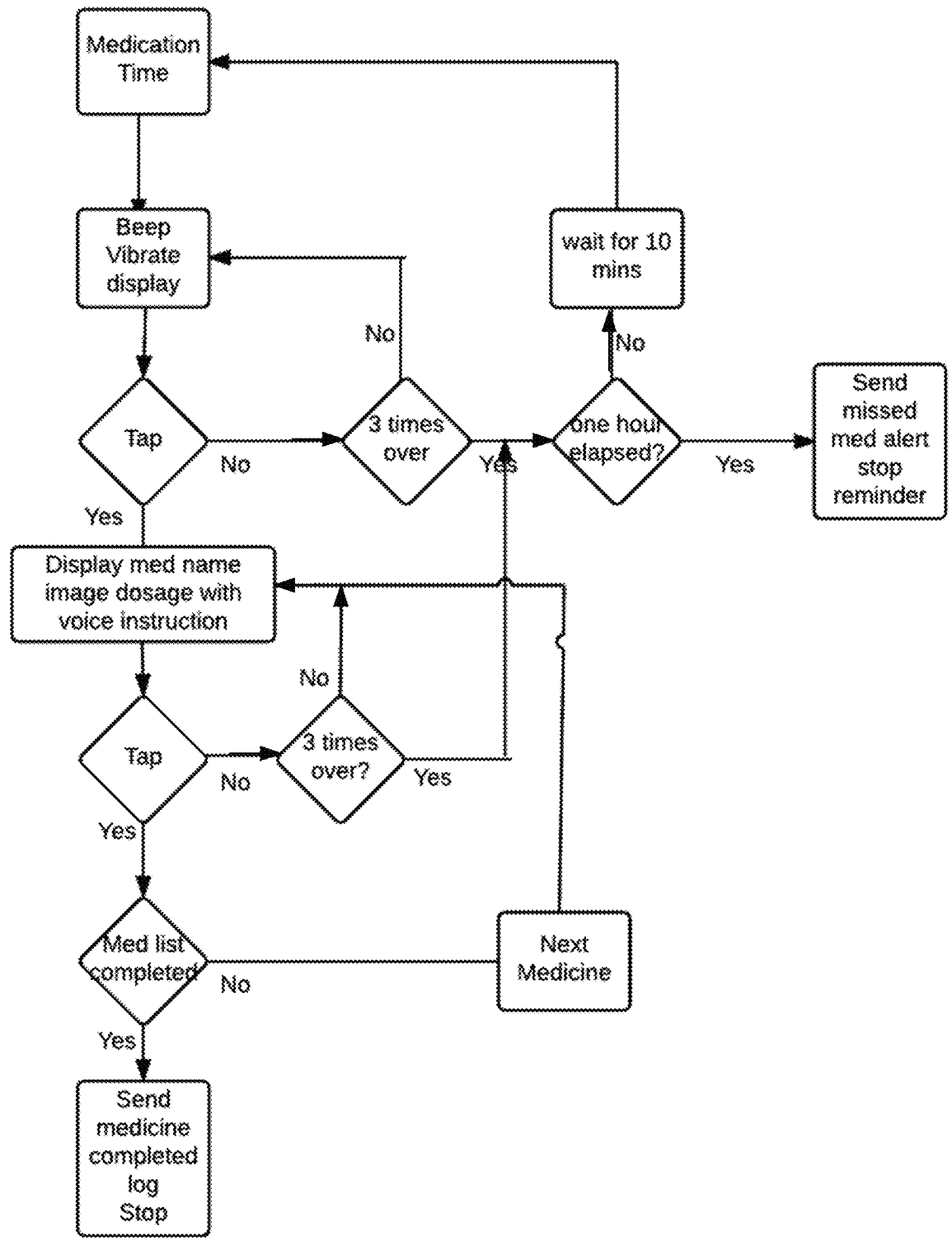
FIG. 5A shows a flow diagram of an example medication reminder process according to the invention.

Once the medication is taken, the patient is required to confirm that the medicine has been taken by tapping on the display screen. If the patient does not confirm taking the medication, the PWD will provide three additional reminders, snooze for 10 minutes and repeat the above-described reminding process. These repeated reminders will continue for one hour (or per physician's' instructions). If even one medication is missed, a missed medication alert listing the missed medicines is generated and sent to the coordinated care platform at the webserver. The flowchart shown in FIG. 5 describes one embodiment of an example medication reminder process.

Figure 6:
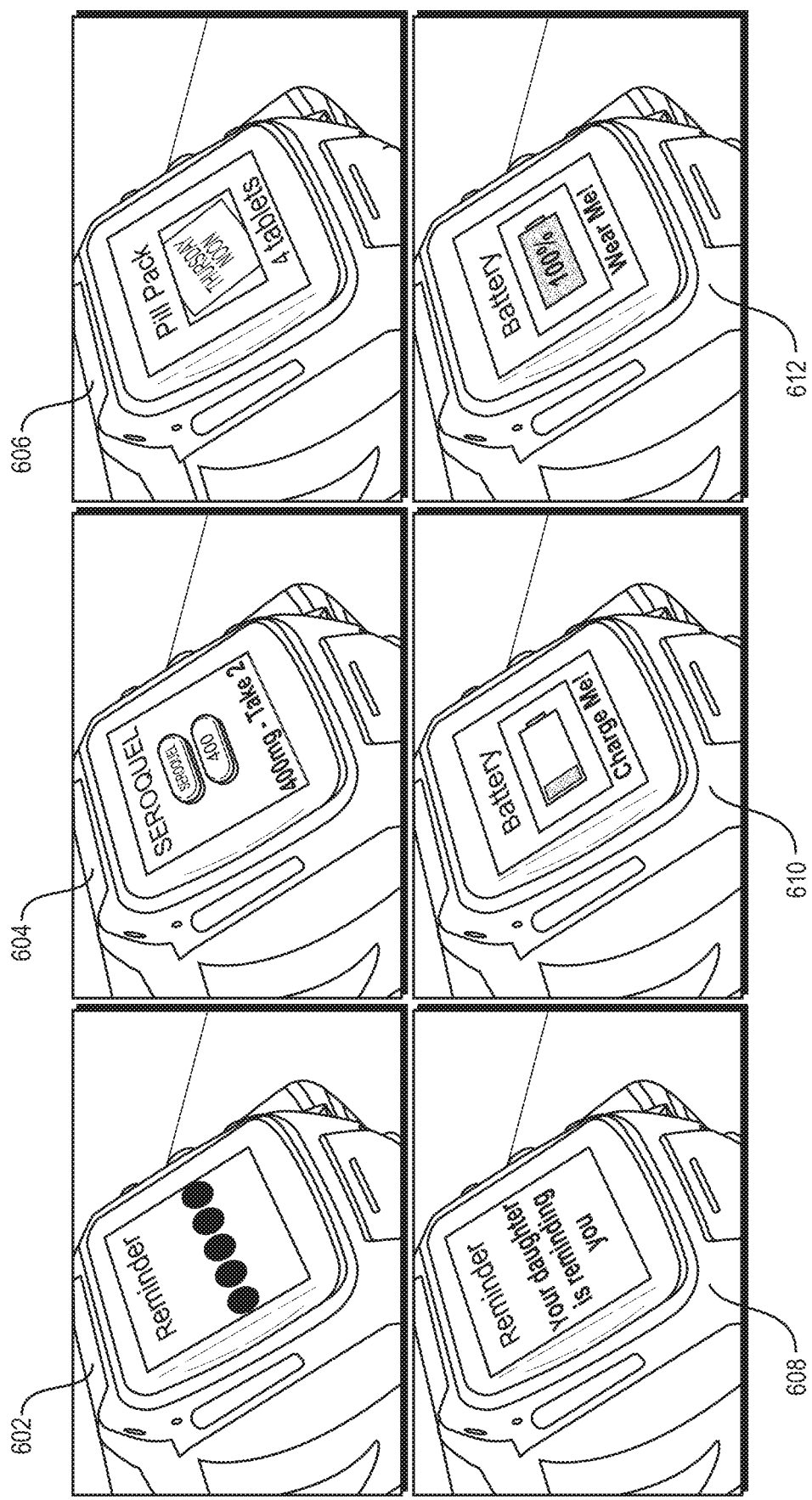
FIG. 6 shows example screen shots of a PWD displaying medication reminder and battery charging reminders.

FIG. 6 provides the example screen shots of a PWD displaying medication reminder and battery charging reminders. An initial reminder screen 602 initially alerts the patient to a medication dosing session, and begins the medication reminder sequence of events. In a first medication screen 604, the PWD shows the medication name (Seroquel), an image of the pill (front and back), and dosage (400 mg—take 2). An alternative medication screen 606 shows a door from a pill pack (Thursday noon) and dosage (4 tablets). Reminder screen 608 shows the PWD displaying another reminder, this time indicating a family member (i.e., daughter). Alert screen 610 shows the PWD displaying a "low battery" alert, requesting the patient to recharge the PWD (i.e., "Charge Me!"), and notification screen 612 notifies the patient that the PWD has been fully charged and is ready to wear again.

When the patient taps the screen, timestamps associated with the taps are recorded and sent to the predictive analytics engine. If the intervals between taps are too short, an alert is raised to the caregiver to check if the patient has taken the scheduled medicines.

Receiving Reminders from Caregivers—Caregivers may be alerted when a patient does not respond to one or more of the scheduled medication reminders. The caregiver can use their mobile app to submit a subsequent reminder to the patient, call the patient, or both.

Providing Activities of Daily Living (ADL) Reminders— Some embodiments may provide reminders to the patient to perform daily activities. Seniors often forget to take their meals on time, drink water or exercise. Lack of water causes dehydration. Exercise is very important for fall prevention, lowering the risk of heart diseases, injury, and elevated blood pressure. Lack of exercise may also lead to increased joint pain. Further, some medications require specific instructions on when to eat food or drink additional water. In some assisted living facilities or independent living communities, the number of nurses to patient ratio is often very small and in general there is not enough nurses to personally remind patients to remind their activities.

The described embodiments provide a convenient way to remind the patient to perform ADLs. These reminder messages can be stored during setup while entering the patient schedule, and the PWD will display those messages on time and get a confirmation that the messages were read. This confirmation may be logged in an activities log, and caregivers can be notified through a status feed. The resulting ADL performance information can be added to behavioral information to be evaluated via the EWPA. For example, a patient that misses meals with increasing frequency may be suffering from worsening memory loss.

Providing Motivational Messages—An embodiment may provide a mechanism where any specialized motivational messages or instructions can be provided to the patient based on a therapy. These messages are displayed based on a schedule configured in the database. Embodiments may include daily motivational messages (with spoken voice playback) encouraging the patient to adhere to their medication schedule and/or treatment program Conducting Real-time Check-In—Real-time, bidirectional communication to survey or check on a patient, such as "Are you doing okay today?" (R U OK) or "How many did you smoke today?"

The "R U OK" communication is designed for seniors who live alone at their homes. The PWD displays the "R U OK" message. If the patient does not answer, an alert is sent to the caregiver or other healthcare provider. The alert can contain additional information including if the PWD is worn, information on the patient's recent activity prior to the alert, and other engagement details.

Requesting HELP—The patient can tap on the PWD 100 to send a HELP message to caregivers, thereby requesting a phone call-back to the PWD 100 (or to an alternative line in the home). Some embodiments of the PWD 100 may require alternative or additional actions from the patient to reduce or avoid false alarms (e.g., double tap or triple tap, or tap followed by a button push).

Call Caregiver/family—By pressing the side button (for example), the patient can initiate a telephone call to the family (or first level responder), through the PWD cellular module 106 and RF interface 108. As with the request for HELP, some embodiments of the PWD 100 may require alternative or additional actions from the patient to reduce or avoid false alarms.

Incoming Calls from caregiver or a set of preprogrammed numbers—The PWD allows authorized numbers (such as caregivers) to call the PWD directly. All other incoming or outgoing calls are blocked to limit potential misuse. Limiting incoming telephone calls may also serve as a comfort factor for the patient, since the patient can feel secure that he or she will not be bothered by annoying telemarketing callers or malicious/fraudulent callers.

Alarms for Low and Full Battery—The PWD lets the patient know, via vibrate, alarm and/or voice prompts, when the energy storage element (e.g. battery) is low, and that the patient should connect to a charger, or when charging is complete Live GPS Tracking & Directions—A geo-fence may be defined (e.g., for early Alzheimer patients) such that if the patient wanders away from his/her home, the PWD detects, using built-in GPS, that the patient is beyond the defined geo-fencing region and alerts their caregiver with accurate location information. In one embodiment, the PWD evaluates its position periodically (e.g., every 15 minutes), and if the PWD moves beyond an established geo-fence, the PWD begins continuous tracking and sends alert to the caregiver along with location information. The tracking continues until the PWD is back within Geo fence range. If the patient plans to intentionally move beyond the geo-fence boundaries (e.g., for a visit to a healthcare provider), the caregiver can disable GPS tracking through the caregiver mobile app until the patient returns to the within the established geo-fence region.

Fall Detection and Emergency Calling—The PWD may detect, using positional sensor input, when a patient has fallen. In response to a detected fall, the PWD may initiate an emergency call to a local call center or to a caregiver. If the patient is able to communicate during the emergency call, the patient may be able to provide information as to subsequent steps. If the patient is not able to communicate, the local call center or caregiver follows a predetermined response protocol for sending help to the patient.

Vitals Collection: In some embodiments, the PWD provides a hub for collecting "vitals" information from devices such as blood glucose monitor, blood pressure monitor and heart rate monitor, and sends the collected data to the backend application of the webserver to report to physicians, hospitals or other healthcare providers. In some embodiments, the information may be collected periodically based on a frequency set in the database.

Patient Profile Manager—This module of the PWD app initializes the PWD database with patient profile information including medication regimen, reminders and other details. Once operational, any updates to the profile information is received and processed by this module.

Battery Alarms—The PWD periodically monitors the state of charge of its energy storage element (i.e., the PWD battery). When the levels reach below a predetermined threshold (e.g., 20%), the PWD provides an audible indication (e.g., beeps) along with a display of the current battery state of charge and a voice instruction to begin recharging the PWD. If the patient does not tap to confirm the recharging notice, the reminders may again be presented periodically, and an alert may also be sent to the caregiver. When the PWD is fully charged, or the PWD recharging source is removed from the PWD, a reminder is sent to the patient instructing him or her to once again wear the PWD. If the PWD is not worn after a few reminders, an alert is sent to the caregiver and the caregiver can call the patient from mobile app or take other action with the patient.

In other embodiments, the PWD may be a commercially available smartwatch, modified to provide the functionality described herein. The commercially available smartwatch may be modified either physically or by having specific apps written for it.

Caregiver Mobile App

The smartphone or tablet application is available for the caregivers and family members, among others, to be able to monitor and communicate in real-time with the patient through the PWD. It should be understood that the concepts described herein may be implemented with alternative components, e.g., a pendant or armband device instead of (or in addition to) the smartwatch. Similarly, the smartphone or tablet application may be implemented on any other platforms suitable for performing the functions and/or capabilities of the described embodiments.

Initial Setup

When the caregiver buys or otherwise initially acquires a PWD for use by a patient, the caregiver can download a caregiver app into their smartphone or tablet from an app store or other source and create an account. The caregiver may then register the patient through the caregiver app, and either enter medication details manually, or download prescription data from an associated pharmacy, provided the caregiver can provide the proper authorization and consent.

When the caregiver enters the medication details manually, they will be prompted to take pictures of the medicine and upload to the coordinated care platform. The caregiver app sequentially guides the caregiver to complete the registration. A caregiver can register and manage multiple patients (e.g., both parents). FIG. 7 illustrates an outline of an example setup procedure of a PWD according to an embodiment. Example caregiver app functionalities, which may be performed by the caregiver app and/or the CSS of the described embodiments, are presented below.

Status feed: The caregivers may receive regular feeds regarding the patient's status, including medication log and other activities such as food, water, exercise, deviation from normal behavior, and GPS tracking.

Alerts and notifications: The caregivers may receive one or more of the following alerts and notifications, which are intended as illustrative examples and are not meant to be limiting: (i) Missed Medication alert, (ii) GPS alert, (iii) Low battery alert, (iv) Watch idle/not worn, (v) Early Warning alerts, (vi) R U OK alert, and (vii) ADL alerts.

When the alerts are received, the caregiver can log in to the coordinated care platform through the caregiver mobile app and review details of the alert. If the review indicates an issue, the caregiver can either send text messages to PWD, or call the PWD, from the caregiver app.

Dashboard: the coordinated caregivers get reports on a weekly basis with details including medication adherence, activities, and R U OK responses. Following reports are provided via dashboard:

Medication adherence logs: number of missed medications in the past week, number of alerts generated for missed medications, number of as needed medications (such as ibuprofen or over the counter medicines), medication adherence trending.

ADL logs: number of missed reminders for food, exercise and water.

R U OK logs: Number of missed R U OK response alerts.

Deviation logs: Deviation or change from normal behavior/activities.

GPS logs: Number of GPS alerts.

Vitals logs: Number of times vitals (e.g., weight, body temperature, blood pressure, heart rate, blood glucose) collected.

Telephone logs: Phone call History and details.

Emergency logs: Number and characteristics of emergency alerts issued.

Webserver

The webserver 106, shown in FIG. 1, implements the coordinated care platform described herein. The webserver 106 includes a backend application and a web-based front end, each of which runs on a processor-based computer system suitable for hosting server software.

The backend application portion of the webserver processes the data sent from the PWD, compares the currently sent PWD data to historical PWD data, and computes one or more trending occurrences based on the comparison. If the backend application detects changes in the patient behavior, with respect to the patient's historical data, the backend generates alerts to caregiver mobile app or hospital dashboard. The coordinated care platform uses JAVA REST API to communicate with web frontend, the pharmacy, the PWD and the caregiver app. The coordinated care platform also uses Google Cloud Messaging (GCM) Service to send messages and alerts. Some embodiments of the coordinated care platform may provide one or more of the following functions:

PWD Management—Includes (i) coordination of the assignment and initialization of PWDs for patients, (ii) registration of PWDs and patients, (iii) the setup by caregivers, (iv) downloading medication information, (v) receiving alerts, (vi) assembling data for the real-time behavioral points that were collected by and sent from the PWD, among others. As described herein, in an example embodiment the number of real-time behavioral points collected by the PWD may exceed 250.

Interface to Caregiver App—Management of caregiver accounts, communication with caregiver app to notify of real-time status information, missed medication alerts, and emergency alerts, among other alerts.

Early Warning Predictive Analytics (EWPA)—Periodical Collection, real-time processing of behavioral points from seniors based on the engagement of the PWD, generation of alerts if anomalies detected from the normal behavioral pattern Storage—some embodiments use a combination of relational (i.e., Structured Query Language—SQL) and Non Structured Query Language (NoSQL) database implementations to store patient profiles, medication regimen and file system to store images of all medications and behavioral data points collected from the patient.

Security—The implementation and maintenance of authentication, authorization and consent forms with respect to all components of the CCS, implementation of a HIPAA compliance platform, and executing verification procedures for caregiver login. Digital signatures such as XML DigSIg or JWT or images will be used for verifying authorization. Other security techniques known in the art may also be used.

Pharmacy Interface—Pharmacy and Electronic Health Records (EHR) interface for one-touch download of prescription information and setup of the PWD. The pharmacies have application programming interfaces (API) to access prescription information. The Fast Healthcare Interoperability Resources (FHIR) describes REST API to get prescription information from EHR. The coordinated care platform may be integrated with pharmacy APIs, so that a pharmacist can download the prescription information, from their pharmacy-based software to the PWD, by clicking "PWD setup" from an application available to the pharmacist (i.e., the pharmacist's access point into the CCS). The pharmacist's app may be a web-based application or an application that is downloaded to the pharmacist's computer platform. Alternatively, as described herein, a caregiver using a caregiver mobile app may coordinate, through the pharmacy, downloading of prescription information to the PWD.

Web Front End—Provides a web-based interface for caregiver login, registration, setup, weekly and on-demand dashboards, to name a few examples.

Real-Time Instrumentation Data and Predictive Analytics

The described embodiments merge the ambulatory assessment and intervention, Ecological Momentary Assessment (EMA) and Ecological Momentary Interventions (EMI), into a single device (PWD). The PWD, coupled with advanced sensors, enables meticulous real-time monitoring to measure a patient's engagement with their treatment and adherence to their medications, by capturing the following instrumentation variables:

- Battery level and time when watch was connected to, and taken out of, a charger.
- Watch movement—sensor output, such as accelerometer, gyroscope, and GPS values, captured periodically, for example every 15 minutes. Other sensor output may also be collected
- Time when a reminder is displayed and time when the reminder is "auto-snoozed" and/or when patient acknowledges taking the medication associated with the reminder.
- Time when medication is displayed and time when it is confirmed as taken or missed.
- Time when a motivational message or survey question is displayed and time when responded.
- Time when patient requests for a HELP callback, when the call is received and its duration.
- Time when patient initiated or received a call to/from the medical staff and its duration Each medication reminder may produce a significant number of behavioral data points to be collected. Medication regimens with several medications therefore multiply those data point quantities. Example medication reminder data points may include (i) time when reminder was displayed, (ii) time when the screen was tapped to listen to the medicine list, (iii) time when the message/display was read, (iv) duration the display was presented, (v) time when the confirmation was tapped, (vi) time when reminder was snoozed, (vii) time when the second reminder was displayed, (viii) time when second time the reminder was auto-snoozed, (ix) time when the third reminder was displayed, (x) time when the alert was sent to the backend Movement of the patient wearing the PWD may also result in a substantial number of behavioral data points to be collected. For example, movement may produce the following data to be collected: (i) time when the patient wears the watch in the morning, (ii) time or times when there is a change in movement, (iii) start time for inactive period (rest, sleep), (iv) end time for inactive period, (v) start time for charging the PWD, (vi) end time for charging the PWD, (vii) start time for idle period (i.e., no movement), (viii) end time for idle period, (ix) start time for rapid movement (e.g., exercise), (x) end time for rapid movement (exercise), (xi) start time when the PWD is not worn by the patient (but is not on the charger), and (xii) time when the PWD is worn again.

Similar data points may be collected with respect to ADL reminders, RU OK responses, PWD cellular telephone usage, among others.

The coordinated care platform can analyze the collected data points to predict potential outcomes. For example, certain combinations of points may be associated with potentially dangerous situations. Examples of such combination of points that can trigger potential danger include: (i) long idle time during an active period, (ii) missing a medication reminder and/or PWD not being worn or being idle during medicine or meal time, (iii) long idle period after rest or nap time, and (iv) unusually long rapid movement period.

Connected Healthcare Platform

The CCS described herein may be used to provide a connected healthcare platform. This connected healthcare platform may connect seniors (i.e., elderly patients), in real-time, with caregivers such as family, physicians, providers and pharmacy. The CCS may alert the caregivers to any anomaly in seniors' health or behavior. The PWD features the following aspects related to a connected healthcare platform:

Medication Reminders & Alerts—to take meds on time, shows medication name, image and dosage with voice instructions, with alerts to clinic on any missed medications Real-time Customizable Interventions—Occasional questions multiple times a day (such as YES/NO, side effects, pain levels) to assess patient's physical and emotional health Patient Safety—fall detection, one-touch phone call to clinic, and water resistant (can be used in the shower or the kitchen)

Early Warning System—collects multiple real-time behavioral engagement and compliance data points every day to assess and alert on any unusual behavior and adverse events.

Real-time Vitals Monitoring—Bluetooth hub to connect to Bluetooth based vital sign monitors such as heart-rate, blood pressure, blood glucose, weight-scale Activity Monitoring—Passively track behavior and environmental exposures in real-time with minimal burden on participants Connected Ecosystem—to clinicians, emergency numbers and trial management system.

Big Data Insights in Real-time—the described embodiments include machine-learning predictive analytics that provide customizable real-time trends, insights and outliers into patient's daily and historical engagement/compliance, health/activity status and response to therapy.

Privacy & Security—HIPAA compliant, encrypted, de-identified database.

Predictive Analytics Early Warning System

As described herein, the PWD may collect a substantial number of real-time behavioral data points every day, to be analyzed by an Early Warning Predictive Analytics (EWPA) machine learning system within the coordinated care platform to alert the caregiver (via our mobile app) in case of any behavioral anomaly. The real-time measurements from the PWD are stored in the backend database. An EWPA predictive algorithm (and its associated model), based on weighted distribution, evaluates historical data trends, predicts the behavior of the patient based on a predetermined number of prior responses and assesses the trending of the patient's compliance. If the adherence decreases (or is tending towards decreased adherence), then a trigger is generated to send alerts to the caregiver to nudge the patient get back on track. The real-time data can be used to predict the patient's adherence behavior and alert nurses or physicians proactively for any timely intervention. Predictive analytics described herein use the real-time data points to calculate a "compliance index" and "engagement index" for each patient.

In some embodiments, the compliance index may be a function of the following values:

Idle time—(During day-time or active time) Use accelerometer readings from the PWD (when not charging) every 15 mins to check if the PWD is moving, or idle (e.g., left on a desk)—assumption is that if the PWD is moving, it is being used and not idle.

Number of Auto-snooze requested—Determine the number of times the patient requested auto-snooze (i.e., activated an appropriate response input to a particular reminder auto-snoozed (means no response) in a day, then aggregate over all days within a predetermined time interval.

Number of Alerts issued—As described in more detail elsewhere herein, if the patient does not respond to a medication reminder within a predetermined time interval, an alert is raised for missed medication. Determine the number of alerts issued within a predetermined time interval.

Charging time—Determine the amount of time the PWD was left on charger—The PWD notifies the patient (i.e., produces beeps) to indicate low charge, full charge, or other charge states, with voice announcement to take it out and wear Battery dead time—Determine the amount of time the PWD remained without charge until it was fully charged and restarted.

In some embodiments, the engagement index may be a function of the following values:

Medication Reminder—Determine the amount of time elapsed between when the reminder was issued (e.g., displayed or sounded) to when the patient acknowledged the reminder. This determination may indicate if the patient is just dismissing the reminder without compliance, or actually taking the medication and then dismissing it.

Daily Motivational Messages and other Reminders—This relates to ADL messages or R U OK messages. Determine the amount of time elapsed between when the message was displayed to when the patient acknowledged the message. This determination may be used to gauge the patient's level of interest in reading the message.

Proof of reading—evaluate PWD position, based on sensor output (e.g., accelerometer, magnetometer, gyroscope, etc.) to see if the PWD has moved to a position or level that evidences the patient reading the PWD display.

Figure 8:
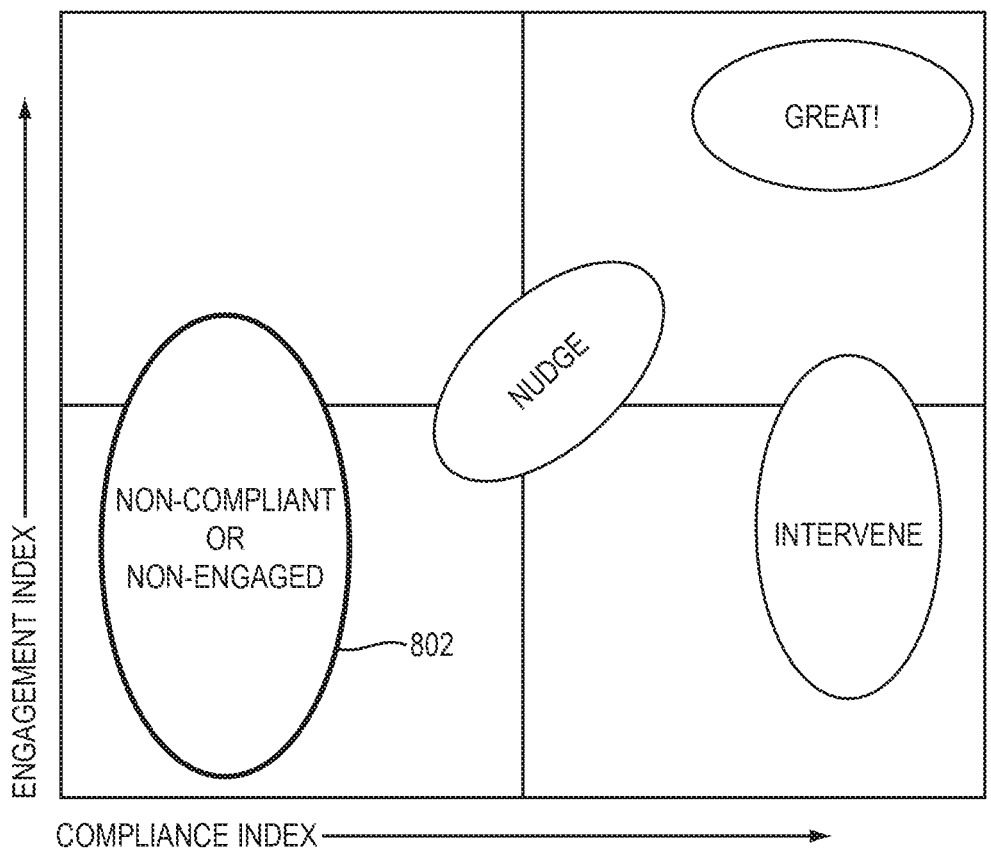
FIG. 8 illustrates an example graph that displays potential actions with respect to combinations of compliance index values and engagement index values.

FIG. 8 illustrates an example graph that displays potential actions with respect to combinations of compliance index values and engagement index values. For example, a combination of the compliance and engagement index falling in the darkly shaded region 802 indicates that it is time to generate an alert.

In one embodiment, the EWPA prediction uses Exponential Weighted Moving Average (EMA) formula for determining indices. The indices are determined every day. Then decreasing weighting is assigned to each datum exponentially, but never becoming zero. Continued decreasing of the EMA value may be indicative of a tendency to deviate from normal behavior.

In one embodiment, the EMA for a series Y may be calculated recursively:

$$S_1 = Y_1, \text{ and for } t > 1, S_t = [\alpha \cdot Y_t][(1-\alpha) \cdot S_{(t-1)}]$$

The coefficient $\alpha$, a constant smoothing factor between 0 and 1, represents the degree of weighting decrease. A higher $\alpha$ discounts older observations faster. $Y_t$ is the value at a time period t, and $S_t$ is the value of the EMA at any time t.

The EWPA prediction uses these indices (and its historical trends) to learn the patient's behavior and help predict and personalize the intervention during follow-up phone calls or in-person meetings.

In an illustrative example, assume that the compliance index maximum value is 10 and the engagement index maximum value is 10. If the collected behavioral data indicates that the patient takes their medicine each time and no alert is raised then the value of 10 is assigned for compliance. If the data indicates that the patient looks at the PWD, reads or hears the instructions, then the engagement index is assigned a value of 10. If the patient scores 10 for both it is great. If, however the patient starts missing medicines and alerts need to be raised, then the compliance value will be some value less than 10, which triggers an alert to be sent to the caregiver. The caregiver may respond to the alert, for example by calling or visiting the patient to determine possible remedial actions.

In another illustrative example, the patient takes their medicine at the first reminder prompt. After a while, the patient's responsiveness slips to require a second reminder (engagement index will be lower) each time. As more time goes by, the patient's responsiveness slips to third reminder. Now looking at historic behavior, the trend is to slowly miss the medicine. The reason could be that the patient is not interested in taking the medicine, or even not hearing or seeing the reminder. This could mean that the patient's health is slowly deteriorating. On the other hand, it could simply be that the patient is busy and knows the third reminder will come. In this case an alert is sent to the caregiver to respond appropriately to the potential non-compliance trending.

Another illustrative example is based on engagement index. In this example, the accelerometer readings are sampled every 15 minutes and the samples will show if there is movement of the patient's hand. During their typical active period, one should see some constant movement. If the patient's resting period gradually lasts longer than usual, or there is no activity for more than an hour during active period, then the patient may be experiencing a health problem. An alert is sent to the caregiver, and the caregiver may respond to the alert, for example by calling or visiting the patient to determine possible remedial actions.

These historical data point trends, when analyzed over the course of the patient's near-term and long-term treatment, help categorize high risk patients (non-engaged or trending towards) versus other patients (reasonably well engaged), prompting a targeted and timely intervention by the medical staff to the high risk patients, thereby contributing to higher adherence rates.

As an example of an alert to family caregiver, suppose the patient wakes up every day between 7:00 AM and 7:15 AM. Then one day, behavioral data from the PWD does not indicate movement even as of 8:00 AM. This data presents an anomaly in behavior and results in an alert to the caregiver to call and check-in with the patient to if a health issue need to be resolved, or if some other acceptable reason for the anomaly exists.

Figure 9:
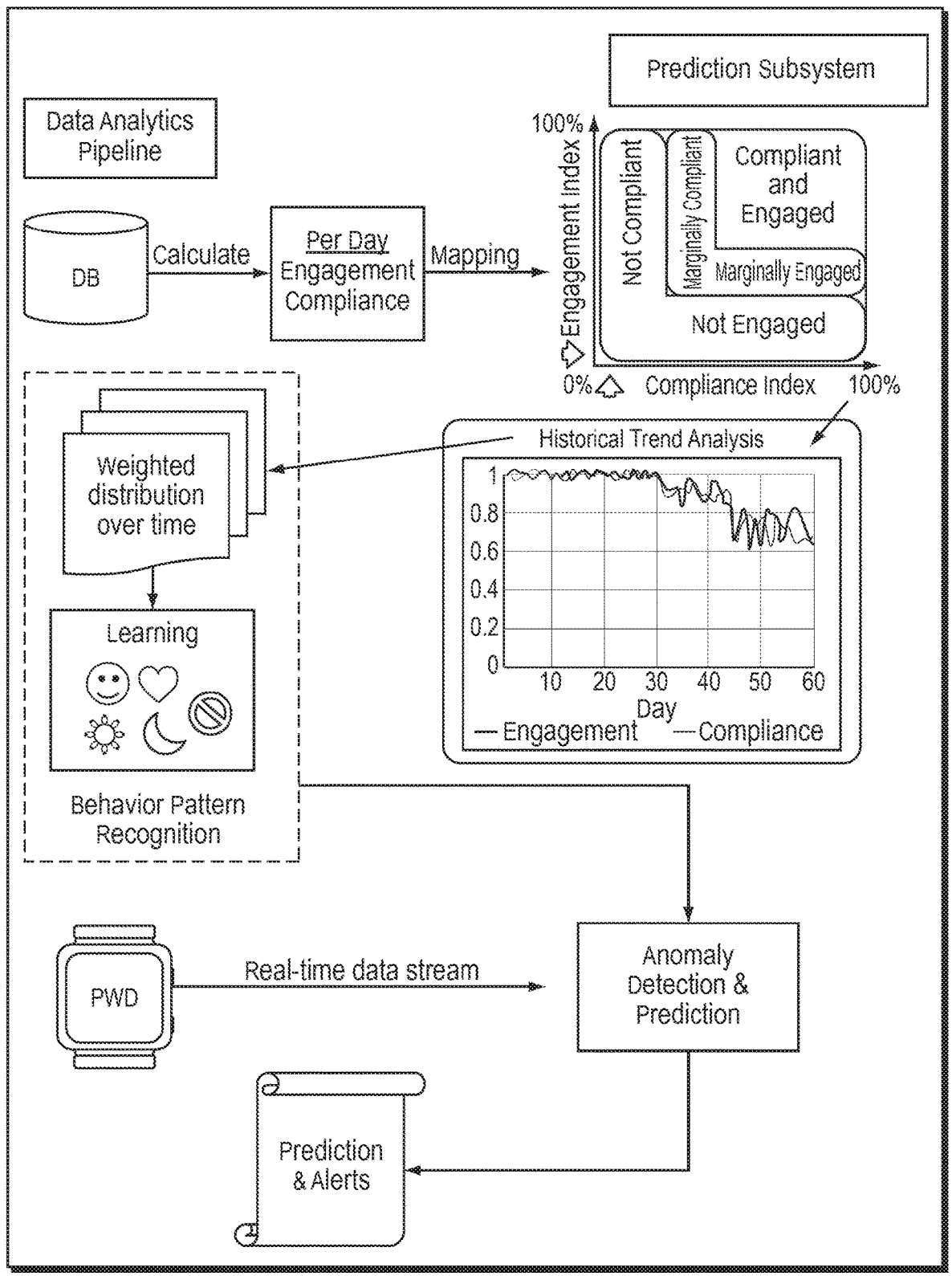
FIG. 9 illustrates an example prediction data pipeline of the CCS predictive analytics platform according to the described embodiments

FIG. 9 illustrates an example prediction data pipeline of the CCS predictive analytics platform according to the described embodiments. The CCS predictive analytics platform collects data in real-time (reported by the PWD periodically, for example every 15 minutes) from all the PWDs deployed. All these data streams are fed into the EWPA prediction system. The backend consists of a Big Data pipeline processor, predictive analytics engine and a user dashboard with reporting engine to provide results in real time to caregivers and various third party healthcare providers. The backend applications are hosted remotely in the webserver (i.e., in the Cloud).

The Coordinated Care Platform enhances the traditional phase 3 clinical trial process by providing a wearable dedicated for real-time monitoring of the patient and their vitals during the trial. The PWD may also serve as a safety alert device with fall detection and emergency calling features. The PWD also passively collects large quantities (but still high quality) of patient's positional data, vital sign data, and physiological data, in real-time. This technology enables increased volume and speed of data collection, as compared to manual methods in traditional clinical trials, leading to further reduced data acquisition costs. This also helps monitor patients' physical and emotional health in real-time outside of the clinic, and could help reduce expensive site visits by the patient.

The backend Big Data data pipelines can be customized to ingest various types of data streams. The (machine learning) AI-based behavioral analytics algorithms with Early Warning System alerts (on potential non-severe Adverse Events) feed on these (raw and derived) data points, making real-time pharmacovigilance possible and improving associated risk mitigation procedures. The metrics, its associated variability levels and acceptable limits can be customized (or personalized) to every trial. The algorithms and insights from Big Data system can effectively help design better follow-up trials. The PWD and the connected ecosystem make outcomes better, faster, and more meaningful, and reduces data collection costs. As compared to using a diary/notebook, the accurate real-time (and on-time) reporting of status and feedback helps increase the efficacy of clinical trial outcomes and success.

While this invention has been particularly shown and described with references to example embodiments thereof, it will be understood by those skilled in the art that various changes in form and details may be made therein without departing from the scope of the invention encompassed by the appended claims.

What is claimed is:

1. A method of supporting adherence, of a user, to a medication regimen, comprising:

by a processor-based wearable computing device that is one of wrist-worn, pendant worn or armband worn, and capable of stand-alone, independent and local execution of processor instruction code and having local data storage configured to store at least medication information and scheduling information, the wearable computing device including a display and an embedded cellular transceiver, the wearable computing device configured to communicate and cooperate with a caregiver component and a webserver component, which together with the wearable computing device comprise a coordinated care system;

storing received medication information that characterizes one or more prescribed medications, including at least medication identification information including at least image information sufficient to render a recognizable image of the medication to be taken, the recognizable image being a photographic image captured from the medication that was filled by a pharmacy, the recognizable image depicting a quantity of the medication to be taken, and prescribed dosing information selectively including (i) when food is required to be taken with, before, or after the medication, (ii) when the medication is to be taken at a specific time, and (iii) personalized voice instructions, comprising a medication name, the quantity of the medication, and/or instructions on how the medication should be taken, that are voiced in a family member's voice, associated with each of the one or more medications, the medication information received from one or both of the caregiver component and the webserver component;

locally generating and storing, by the wearable computing device and independent of network connectivity, a visually-renderable reminder schedule based on the received medication information, prescribed dosing information, and a meal schedule associated with the user, the reminder schedule generated to coordinate the meal schedule with when food is required to be taken with the medication and/or when the medication is to be taken at a specific time;

displaying (i) the medication identification information including at least the recognizable image of the medication and (ii) dosing information selectively including when food is required to be taken with, before or after the medication, and when the medication is to be taken at a specific time, associated with at least one of the one or more medications according to the reminder schedule;

generating, based on the reminder schedule and independent of network connectivity, an initial notification indicating that the medication identification information is being displayed;

monitoring a response input instrumentality configured to receive a response indicating that the at least one of the one or more medications has been administered;

for each of the one or more medications displayed, generating a medication status describing that either (i) the medication has been administered or (ii) the response has not been received; and when the medication status indicates that the response has not been received, (i) activating a camera integrated into the wearable computing device, and (ii) conveying the medication status to a caregiver, and receiving a subsequent reminder from the caregiver in response to the conveyed medication status.

2. The method of claim 1, further including generating a reminder notification when the medication status indicates that the response has not been received, by:
- re-displaying medication identification information and dosing information associated with one or more medications referenced in the reminder;
- generating a subsequent notification indicating that the medication identification information is being displayed;
- monitoring the response input instrumentality; and
- for each of the one or more medications referenced in the reminder, generating an updated medication status describing that either (i) the medication has been administered or (ii) the response has not been received.

3. The method of claim 2, further including repeating the reminder notification periodically until:
- (i) all of the at least one medications have been administered; or
- (ii) a predetermined time period has elapsed since generation of the initial notification.

4. The method of claim 3, further including providing the reminder notification by playing a voice recording generated by a caregiver.

5. The method of claim 3, further including repeating the reminder notification at intervals of about 10 minutes.

6. The method of claim 3, further including notifying a caregiver after the predetermined time period has elapsed.

7. The method of claim 1, further including automatically accepting an incoming communication conveying the subsequent reminder, generating a subsequent notification indicating that the medication identification information is being displayed, and monitoring the response input instrumentality configured to receive a response indicating that the at least one of the one or more medications has been administered.

8. The method of claim 7, further including automatically accepting an incoming telephone call when the incoming communication acceptance input instrumentality does not receive an accept response within a predetermined time interval.

9. The method of claim 7, wherein the incoming communication is a real-time communication configured to one or both of (i) survey a patient and (ii) check in on the patient.

10. The method of claim 1, further including automatically connecting to a healthcare device, receiving health information from the healthcare device, the health information comprising one or more of (i) blood glucose, (ii) blood pressure, and (iii) heart rate, storing the health information and forwarding the health care information to a caregiver.

11. The method of claim 1, wherein the identification information and dosing information includes an image associated with the at least one of the one or more medications, the image including a depiction of a vehicle by which the medication is administered, the vehicle instantiated a number of times corresponding to the dosing information.

12. The method of claim 1, further including activating a camera integrated into the wearable computing device, the activating occurring in response to a camera stimulus provided by the caregiver.

13. The method of claim 12, wherein the camera stimulus includes one or more of (i) a camera activation communication received from a caregiver, (ii) the medication status indicates that the response has not been received.

14. The method of claim 1, further including synchronizing the wearable computing device by receiving and storing updated medication information.

15. The method of claim 1, further including determining geolocation of the wearable computing device in relation to a predetermined area, and notifying a caregiver when the geolocation is determined to be outside of the predetermined area.

16. The method of claim 1, further including:
- (i) detecting that the user has fallen by analyzing an output of one or more accelerometers embedded in the wearable computing device;
- (ii) notifying a caregiver upon detecting that the user has fallen.

* * * * *